(12) United States Patent
Sosiak

(10) Patent No.: US 6,425,392 B1
(45) Date of Patent: Jul. 30, 2002

(54) BREATH-ACTIVATED METERED-DOSE INHALER

(75) Inventor: Alexander K. D. Sosiak, Queens, NY (US)

(73) Assignee: Clavius Devices, Inc., Rego Park, NY (US)

( * ) Notice: Subject to any disclaimer, the term of this patent is extended or adjusted under 35 U.S.C. 154(b) by 0 days.

(21) Appl. No.: 09/411,740

(22) Filed: Oct. 1, 1999

Related U.S. Application Data

(62) Division of application No. 09/099,362, filed on Jun. 18, 1998.

(51) Int. Cl.⁷ .................................. A61M 11/00
(52) U.S. Cl. .................. 128/200.23; 128/200.14; 128/200.24; 128/203.12; 128/203.21
(58) Field of Search .................. 128/200.14, 200.19, 128/200.22, 200.24, 202.21, 202.28, 203.11, 203.12, 203.15, 203.25, 205.11, 206.29, 200.23; 131/270–273; 482/13; 600/530–533, 573

(56) References Cited

U.S. PATENT DOCUMENTS

| | | |
|---|---|---|
| 3,456,645 A | 7/1969 | Brock |
| 3,565,070 A | 2/1971 | Hanson |
| 3,593,710 A * | 7/1971 | Eichelman et al. .... 128/204.23 |
| 3,814,297 A | 6/1974 | Warren |
| 4,524,769 A * | 6/1985 | Wetterlin ............... 128/203.15 |
| 4,648,393 A | 3/1987 | Landis et al. |
| 4,664,107 A | 5/1987 | Wass |
| 4,735,217 A * | 4/1988 | Gerth et al. ............... 131/273 |
| 4,796,614 A | 1/1989 | Nowacki et al. |
| 4,803,978 A | 2/1989 | Johnson, IV et al. |
| 4,955,371 A | 9/1990 | Zamba et al. |

(List continued on next page.)

FOREIGN PATENT DOCUMENTS

| | | | | |
|---|---|---|---|---|
| CA | 699313 | * | 12/1964 | ............ 128/200.23 |
| GB | 1190997 | | 5/1990 | |
| GB | 2240930 A | | 8/1991 | |
| GB | 2 279 879 | | 1/1995 | |
| WO | PCT/US84/01721 | | 5/1985 | |
| WO | PCT/SE90/00137 | | 9/1990 | |
| WO | PCT/GB90/01665 | | 5/1991 | |
| WO | PCT/CH91/00156 | | 2/1992 | |
| WO | PCT/GB91/01868 | | 5/1992 | |
| WO | PCT/US92/01815 | | 9/1992 | |
| WO | PCT/US92/02555 | | 10/1992 | |
| WO | WO 92/17231 | * | 10/1992 | ............ 128/200.14 |

OTHER PUBLICATIONS

International Search Report (6 pages), Oct. 22, 1999, PCT/US99/13354.

Abisheganaden J., Sin Fai Lam KN, Lim T.K., *A Profile Of Acute Asthma Patients Presenting To The Emergency Room*, Singapore Med. Journal, Jun. 1996, 37(3), 252–254.

Amirav I., Goren A., Pawlowski N.A., *What Do Pediatricians In Training Know About The Correct Use Of Inhalers And Spacer Devices*? Journal of Allergy and Clinical Immunology, Oct. 1994, 94(4), 669–675.

(List continued on next page.)

*Primary Examiner*—John G. Weiss
*Assistant Examiner*—Joseph F. Weiss, Jr.
(74) *Attorney, Agent, or Firm*—Morgan & Finnegan, LLP

(57) ABSTRACT

The invention provides a device for dispensing medication in the respiratory system, with provision for breath-activation; open and closed-mouth technique; recording and control of dosage; and enhanced atomization of liquid medication. This is accomplished with a device that uses a medication canister with an integral battery and circuitry, the battery providing power for electro-mechanical activation, counting medication dosage used or remaining, and controlling device activation. The invention has capability for use with dry and wet medication, and is easily cocked with a simple manual action.

13 Claims, 6 Drawing Sheets

U.S. PATENT DOCUMENTS

| | | | |
|---|---|---|---|
| 5,054,477 A | | 10/1991 | Terada et al. |
| 5,060,643 A | | 10/1991 | Rich et al. |
| 5,209,225 A | | 5/1993 | Glenn |
| 5,217,004 A | | 6/1993 | Blasnik et al. |
| 5,221,025 A | * | 6/1993 | Privas .......................... 222/1 |
| 5,284,133 A | | 2/1994 | Burns et al. |
| 5,318,015 A | * | 6/1994 | Mansson et al. ....... 128/200.22 |
| 5,322,057 A | * | 6/1994 | Raabe et al. ........... 128/203.12 |
| 5,347,998 A | | 9/1994 | Hodson et al. |
| 5,363,842 A | | 11/1994 | Mishelevich et al. |
| 5,419,315 A | | 5/1995 | Rubsamen |
| 5,435,297 A | | 7/1995 | Klein |
| 5,447,150 A | * | 9/1995 | Bacon ................... 128/200.14 |
| 5,450,336 A | | 9/1995 | Rubsamen et al. |
| 5,458,135 A | * | 10/1995 | Patton et al. .......... 128/200.14 |
| 5,479,920 A | * | 1/1996 | Piper et al. ............ 128/204.23 |
| 5,487,378 A | * | 1/1996 | Robertson et al. ..... 128/200.16 |
| 5,497,764 A | | 3/1996 | Ritson et al. |
| 5,507,278 A | | 4/1996 | Karell |
| 5,507,281 A | | 4/1996 | Kuhnel et al. |
| 5,509,404 A | | 4/1996 | Lloyd et al. |
| 5,511,540 A | * | 4/1996 | Bryant et al. .......... 128/200.23 |
| 5,520,166 A | | 5/1996 | Ritson et al. |
| 5,542,410 A | | 8/1996 | Goodman et al. |
| 5,544,647 A | * | 8/1996 | Jewett et al. .......... 128/200.23 |
| 5,558,085 A | | 9/1996 | Rubsamen et al. |
| 5,571,246 A | * | 11/1996 | Alldredge .............. 128/200.23 |
| 5,596,982 A | | 1/1997 | Blaha-Schnabel |
| 5,608,647 A | * | 3/1997 | Rubsamen et al. .... 128/204.21 |
| 5,617,844 A | | 4/1997 | King |
| 5,617,845 A | | 4/1997 | Poss et al. |
| 5,622,162 A | | 4/1997 | Johansson et al. |
| 5,622,163 A | | 4/1997 | Jewett et al. |
| 5,655,516 A | | 8/1997 | Goodman et al. |
| 5,666,945 A | * | 9/1997 | Davenport ............. 128/200.14 |
| 5,676,129 A | * | 10/1997 | Rocci, Jr. et al. ....... 128/200.23 |
| 5,692,492 A | * | 12/1997 | Bruna et al. ........... 128/200.23 |
| 5,694,919 A | | 12/1997 | Rubsamen et al. |
| 5,694,920 A | * | 12/1997 | Abrams et al. ........ 128/200.16 |
| 5,701,886 A | * | 12/1997 | Ryatt ..................... 128/203.12 |
| 5,709,202 A | | 1/1998 | Lloyd et al. |
| 5,718,222 A | | 2/1998 | Lloyd et al. |
| 5,724,957 A | | 3/1998 | Rubsamen et al. |
| 5,735,263 A | | 4/1998 | Rubsamen et al. |
| 5,743,250 A | | 4/1998 | Gonda et al. |
| 5,743,252 A | | 4/1998 | Rubsamen et al. |
| 5,755,218 A | | 5/1998 | Johansson et al. |
| 5,809,996 A | * | 9/1998 | Allredge ............... 128/200.23 |
| 5,819,726 A | | 10/1998 | Rubsamen et al. .... 128/200.14 |
| 5,823,434 A | * | 10/1998 | Cooper ................... 239/102.2 |
| 5,826,571 A | * | 10/1998 | Casper et al. .......... 128/200.23 |
| 5,860,416 A | * | 1/1999 | Howlett ................. 128/200.23 |
| 5,938,118 A | * | 8/1999 | Cooper ................... 239/102.2 |
| 6,009,869 A | * | 1/2000 | Corbeil .................. 128/200.21 |
| 6,014,972 A | * | 1/2000 | Sladek ................... 128/203.12 |
| 6,029,660 A | * | 2/2000 | Calluaud et al. ....... 128/203.12 |
| 6,044,841 A | * | 4/2000 | Verdun et al. ......... 128/200.18 |
| 6,055,979 A | * | 5/2000 | Fuchs .................... 128/203.15 |
| 6,138,669 A | * | 10/2000 | Rocci, Jr. et al. ....... 128/200.23 |
| 6,260,549 B1 | * | 7/2001 | Sosiak ................... 128/200.23 |

OTHER PUBLICATIONS

Atsuta J., Takao F., Kousei I., *The Relationship Of Eosinophil Viability Enhancing Activity In Sputum And Clinical Symptoms in Asthma*, Areugi, Oct. 1996, 45(10), 1088–1097.

Barry P.W., O'Callaghan C., *Inhalational Drug Delivery From Seven Different Spacer Devices*, Thorax, Aug. 1996, 51(8), 835–840.

Barry P.W., O'Callaghan C., *The Effect Of Delay, Multiple Actuations And Spacer Static Charge On The In Vitro Delivery Of Budesonide From The Nebuhaler*, British Journal of Clinical Pharmacology, Jul. 1995, 40(1). 76–78.

Barry P.W., O'Callaghan C., *Multiple Actuations Of Salbutamol MDI Into A Spacer Device Reduce The Amount Of Drug Recovered In Respirable Range* European Respiratory Journal, Sep. 1994, 7(9), 1707–1709.

Battistini A., *The Best Way To Apply Aerosol Therapy*, Pediatric Med. Chir, Mar.–Apr. 1995, 17(2), 97–103.

Benjaponpitak S., Kraisaarin C., Direkwattanachai C., Sasissakunporn C., *Incorrect Use Of Metered Dose Inhalers By Pediatric Residents*, Journal of the Medical Association of Thailand, Feb. 1996, 79(2), 122–126.

Bisgaard H., Anhoj J., Klug B., Berg E., *A Non–Electrostatic Spacer For Aerosol Delivery*, Arch. of Dic. Children, Sep. 1995, 73(3), 226–230.

Boccuti L., Celano M., Geller R.J., Phillips K.M., *Development Of A Scale To Measure Children's Metered Dose Inhaler And Spacer Technique*, Annals of Allergy, Asthma and Immunology, Sep., 1996, 77(3), 217–221.

Borgstrom L., Derom E., Stahl E., Wahlin–Boll E., Pauwels R., *The Inhalation Device Influences Lung Deposition And Bronchodilating Effect Of Terbutaline*, American Journal of Respiratory and Critical Care Medicine, May 1996, 153(5), 1636–1640.

Boulet L.P., d'Amours P., Berube D., Rouleau M., Parent J.G., Pelletier C. & Touchette C., *Update On Inhalation Therapy In Asthma And Obstructive Bronchopulmonary Diseases*, Union Med. Canada, Jan. 1994, 123(1), 23–31.

Connolly M.J., *Inhaler Technique Of Elderly Patients: Comparison Of Metered Dose Inhalers And Large Volume Spacer Devices*, Age Ageing, May 1995, 24(3), 190–192.

Cowley G., & Underwood A., *Why Ebonie Can't Breathe*, Newsweek, May 26, 1997, 129(21), 58–64.

Everard M.L., Devadason S.G., Summers Q.A., LeSouef P.N., *Factors Affecting Total And "Respirable" Dose Delivered By Salbutamol Metered Dose Inhaler*, Thorax, Jul. 1995, 50(997), 746–749.

Farr S.J., Rowe A.M., Rubsamen R., Taylor G., *Aerosol Deposition In The Human Lung Following Administration From A Microprocessor Controlled Pressurized Metered Dose Inhaler*, Thorax, Jun. 1995, 50(6),639–644.

Goldberg S., Algur N., Levi M., Brukheimer E., Hirsch H.J., Branski D., Kereem E., *Adrenal Suppression Among Asthmatic Children Receiving Chronic Therapy With Inhaled Corticosteroid With And Without Spacer Device*, Annals of Allergy, Asthma and Immunology, Mar. 1996, 76(3), 234–238.

Goodman D.E., Israel E., Rosenberg M., Johnston R., Weiss St., Drazen J.M., *The Influence Of Age, Diagnosis, And Gender On Proper Use Of Metered–Dose Inhalers*, American Journal of Respiratory and Critical Care Medicine, Nov. 1994, 150(5 Part I), 1256–1261.

Gray S.L., Nance A.C., Williams D.M., Pulliam C.C., *Assessment Of Interrater Reliability In The Evaluation Of Metered Dose Inhaler Technique*, Chest, Mar. 1994, 105(3), 710–714.

Gray S.L., Williams D.M., Pulliam C.C., Sirgo M.A., Bishop A.L., Donohue J.F., *Characteristic Predicting Incorrect Metered Dose Inhaler Technique In Older Subjects*, Archives of Internal Medicine, May 1996, 156(9), 984–988.

Grossman J., *The Evolution Of Inhaler Technology*, Journal of Asthma, 1994, 31(1), 55–64.

Hampson N.B., Mueller M.P., *Reduction In–Patient Timing Errors Using A Breath–Activated Metered Dose Inhaler*, Chest, Aug. 1994, 106(2), 462–465.

Hanania N.A., Wittman R., Kesten S., Chapman K.R., *Medical Personnel's Knowledge Of And Ability To Use Inhaling Devices: Metered Dose Inhalers, Spacing Chambers, And Breath–Actuated Dry Powder Inhalers*, Chest, Jan. 1994, 105(1), 111–116.

Hartert T.V., Windom H.H., Peebles R.S. Jr., Freidhoff L.R., Togias A., *Inadequate Outpatient Therapy For Patients With Asthma Admitted To Two Urban Hospitals*, American Journal of Medicine, Apr. 1996, 100(4), 386–394.

Hindle M., Newton D.A., Chrystyn H., *Dry Powder Inhalers Are Bioequivalent To Metered Dose Inhalers*, Chest, Mar. 1995, 107(3), 629–633.

Hira H.S., *Faulty Use Of Metered Dose Inhalers By Physicians*, Journal of Assoc. of Physicians in India, Jul. 1994, 42(7), 524–525.

Iula, A.K., Flynn C.L., Delucca F., *Comparative Study Of The In Vitro Dose Delivery And Particle Size, Distribution, Characteristics Of An Azmacort Metered–Dose Inhaler In Combination With Four Different Spacer Devices*, Current Therapeutic Research, Aug. 1997, 58(8), 544–554.

Jones J.S., Holstege C.P., Riekse R., White L., Bergquist T., *Metered–Dose Inhalers: Do Emergency Health Care Providers Know What To Teach?* Annals of Emergency Medicine, Sep. 1995, 26(3), 308–311.

Kleerup E.C., Tashkin D.P., Cline A.C., Aakholm B.P., *Cumulative Dose–Response Study Of Non–CFC Propellant HFA 134a Salbutamol Sulfate Metered Dose Inhaler In Patients With Asthma*, Chest, 1996, 109(3), 702–707.

Larsen J.S., Haaahn M., Ekholm B., Wick K.A., *Evaluation Of Conventional Press–And–Breathe Metered Dose Inhaler Technique In 501 Patients*, Journal of Asthma, 1994, 31(3), 193–199.

Levitt M.A., Gambrioli E.F., Fink J.B., *Comparative Trial Of Continuous Nebulization Versus Metered–Dose Inhaler In The Treatment Of Acute Bronchospasm*, Annals of Emergency Medicine, Sep. 1995, 26(3), 273–277.

Majumdar S.P., Kumar T.R., *Inhalation Steroids, Some Aspects And Ways In The Management Of Asthma*, Journal of Indian Medical Association, Jul. 1994, 92(7), 233–234.

Milgrom H., Bender B., Ackerson L., Bowry P., Smith B., Rand C., *Noncompliance And Treatment Failure In Children With Asthma*, Journal of Allergy and Clinical Immunology, Dec. 1996, 98(6 Part I), 1051–1057.

Miller N.C., Purrington A.M., *A Cascade Impactor Entry Port For MDI Sprays With Collection Characeristics Imitating A Physical Model Of The Human Throat*, Pharm. Research, Mar. 1996, 13(3), 391–397.

National Institutes of Health: National Heart, Lung, and Blood Institute. *Guidelines For The Diagnosis And Management Of Asthma*, Jul. 1997, Bethesda Maryland, NIH Publication No. 97–44051, 1–154.

Negro J.M., Sarrio E., Millares J.C., Hernandez J., Garcia Selles F.J., Pagan J.A., Lopez Sanchez J.D., *Treatment Of Asthma Using Aerosols*, Allergol Immunopathol. Jul.–Aug. 1996, 24(4), 139–145.

Nelson H.S., Loft D.T., *Aerochamber Or By Metered Dose Inhaler Alone*, Annals of Allergy, Apr. 1994, 72(4), 337–340.

Newman S.P., Sted K.P., Resader S.J., Hooper G., Zierenberg B., *Efficient Delivery To The Lungs Of Flunisolide Aerosol From A New Portable Hand–Held Multi–Dose Nebulizer*, Journal of Pharm. Science, Sep. 1996, 85(9), 960–964.

Newman S.P., Weisz A.W., Talaee N., Clarke S.W., *Improvement Of Drug Delivery With A Breath–Activated Pressurised Aerosol For Patients With Poor Inhaler Technique*, Thorax, 1991, 4(46), 712–716.

Niven B.B., *Floating Doesn't Count. Letters to the Editior;* Clinician Reviews, Aug. 1997, 7(8), 27.

O'Callaghan C., Cant M., Robertson C., *Deliver of Beclomethasone Dipropionate From A Spacer Device: What Dose Is Available For Inhalation*, Thorax, Oct. 1994, 49(10), 961–964.

Obata T., Fujikaawaa M., Obata Y., Obata J., *Evaluations Of A Specified Number Of Inhalations And How To Assess The Contents In Metered Dose Inhalers*, Areugi, Oct. 1996, 45(10), 1089–1097.

Ojima F., Toyoguchi T., Shoji T., Nakagawa Y., *Comparison By Twin Impinger Of The Distribution Patterns Of Two Beclomethasone Dipropionate Metered Dose Inhalers And Of Two Spacer Devices*, Areugi, Jun. 1995, 44(6), 586–592.

Pauwels R.A., Hargreave F.E., Camus P., Bukoski M., Stahl E., *A 1–Year Study Of Turbohaler Vs Pressurized Metered Dose Inhaler In Asthmatic Patients*, Chest, Jul. 1996, 110(1), 53–57.

Perring S., Summers Q., Fleming J.S., Nassim M.A., Holgate St., *A New Methods Of Quantification Of The Pulmonary Regional Distribution Of Aerosols Using Combined CT And SPECT And Its Application to Nedocromil Sodium Administered By Metered Dose Inhaler*, British Journal of Radiology, Jan. 1994, 67(793), 46–53.

Peterferund R.A., Niven R.W., Kacmarek R.M., *Syringe–Actuated Metered Dose Inhalers: A Quantitative Laboratory Evaluation Of Albuterol Delivery Through Nozzle Extensions*, Anesthesia Analgesia, Mar. 1994, 78(3), 554–558.

Rebuck D., Dzyngel B., Khan K., Kesten R.N., Chapman K.R., *The Effect Of Structured Versus Conventional Inhaler Education In Medical Housestaff*, Journal of Asthma, 1996, 33(6), 385–393.

Resnick D.J., Gold R.L., Lee–Wong M., Feldman B.R., Ramakrishnana R., Davis W.J., *Physicians' Metered Dose Inhaler Technique After a Single Teaching Session*, Annals of Allergy, Asthma Immunology, Feb. 1996, 76(2), 145–148.

Rokosky J.M., *Misuse Of Metered Dose Inhalers: Helping Patient Get It Right*, Home Healthcare Nurse, Jan. 1997, 15(1), 13–21/quiz 23–24.

Selroos O., Lofross A.B., Pietinaalho A., Riska H., *Comparison Of Terbutaline And Placebo From A Pressurised Metered Dose Inhaler And A Dry Powder Inhaler In A Subgroup Of Patients With Asthma*, Thorax, Dec. 1994, 49(12), 1228–1230.

Shah S.P., Ailani R.K., *Metered Dose Inhalers—Practical Considerations and Correct Use*, Journal of Assoc. of Physicains in India, Jul. 1994, 42(7), 520.

Shaheen M.Z., Aayres J.G., Benincasa C., *Incidence Of Acute Decreases In Peak Expiratory Flow Following The Use Of Metered Dose Inhalers In Asthmatic Patients*, European Respiratory Journal, Dec. 1994, 7(12), 2160–2164.

Shrestha M., Parupia H., Andrews B., Kim S.W., Martin M.S., Park D.I., Gee E., *Metered Dose Inhaler Technique Of Patients In An Urban ED: Prevalence Of Incorrect Technique And Attempt At Education*, American Journal of Emergency Medicine, Jul. 1996, 14(4), 380–384.

Thompson J., Irvine T., Grathwohl K., Roth B., *Misuse Of Metered–Dose Inhalers In Hospitalized Patients*, Chest, Mar. 1994, 105(3), 715–717.

Vasquez Acevess M.L., Gomez Castillo C.A., Martinez Cairo S., Cisneros Gonzalez N., *Effect On FEV1 Induced By The Administration Of Salbutamol With Aerochamber And Metered Dose Inhaler*, Rev. Alergy Mexico, May–Jun. 1995, 42(3), 414–444.

Williamson I.J., Matusiewicz Sp., Brown P.H., Greening A.P., Crompton G.K., *Frequency Of Voice Problems And Cough In Patients Using Pressurized Aerosol Inhalers Steroid Preparations*, European Respiratory Journal, Apr. 1995, 8(4), 590–592.

\* cited by examiner

BREATH-ACTIVATED METERED-DOSE INHALER

This is a divisional of prior application Ser. No. 09/099,362 Jun. 18, 1998.

BACKGROUND OF THE INVENTION

1. Field of the invention

This invention relates to a device for dispensing medication in the respiratory tract, and more particularly to a breath-activated device with provision for open and closed-mouth techniques, electronic measurement and control, and electro-mechanical activation.

2. Background

Asthma is a disease that is a growing epidemic in this country and affects 14.6 million Americans, including 5 million children. (Cowley G., & Underwood A., *Why Ebonie Can't Breathe,* Newsweek, May 26, 1997, 129(21), 58–64). According to the American Lung Association, the number of sufferers has risen by 61 percent since the early 1980's. Id. The death toll from asthma has also nearly doubled, to a tragic 5000 per year. Id. These statistics are appalling considering that today, physicians have many more types of medications available for treatment.

The majority of medications for asthma treatment are intended for delivery to the lung. In this way, the drug can most quickly reverse the acute breathing problem that asthma causes to the sufferer. Delivery of medication directly to the lung also allows use of less drug, minimizing systemic side effects, since only the lung is affected by the disease.

Techniques of medication delivery to the lungs for asthma sufferers have a long history and have seen many improvements. However, significant disadvantages remain in the delivery systems in use today. The nineteenth century saw the invention and use of the glass bulb nebulizer. (Hampson N. B., Mueller M. P., *Reduction In-Patient Timing Errors Using A Breath-Activated Metered Dose Inhaler,* Chest, August 1994, 106(2), 462–465). At the turn of the century, cigarettes laced with atropine were used. Id. The first pressure metered dose inhaler (MDI) was introduced in 1956. (Newman S. P., Weisz A. W., Talaee N., Clarke S. W., *Improvement Of Drug Delivery With A Breath-Activated Pressurized Aerosol For Patients With Poor Inhaler Technique,* Thorax, 1991, 4(46), 712–716). Though bulky, noisy and cumbersome to use, the first breath activated aerosol inhaler was introduced a number of years ago. Id. In an effort to improve medication delivery, spacer devices used with MDI's were introduced in the 1970's. (Iula, A. K., Flynn C. L., Delucca F., *Comparative Study Of The In Vitro Dose Delivery And Particle Size, Distribution, Characteristics Of An Azmacort Metered-Dose Inhaler In Combination With Four Different Spacer Devices,* Current Therapeutic Research, August 1997, 58(8), 544–554).

Nebulizers have been the treatment mainstays for acute asthmatics in emergency departments. Nebulizers offer an advantage of delivering a higher dose of medication to the lung than MDI's (Newman S. P., Sted K. P., Resader S. J., Hooper G., Zierenberg B., *Efficient Delivery To The Lungs Of Flunisolide Aerosol From A New Portable Hand-Held Multi-Dose Nebulizer,* Journal of Pharm. Science, September 1996, 85(9), 960–964) and once set up, the nebulizer requires no training and minimal cooperation from the patient. With a nebulizer, there is also less deposition of medication in the oropharynx as compared to MDI's. (Battistini A., *The Best Way To Apply Aerosol Therapy,* Pediatric Med. Chir, March–April 1995, 17(2), 97–103). The deficiencies of nebulizers are that they are expensive, time consuming, bulky, non-portable, and usually AC current-dependent. A nebulizer also takes minutes to deliver its dose, and needs considerable time to set-up for that delivery. The output of nebulizers is device-dependent and there is significant inter-nebulizer and intra-nebulizer output variance. (National Institutes of Health: National Heart, Lung, and Blood Institute. *Guidelines For The Diagnosis And Management Of Asthma,* July 1997, Bethesda, Md., NIH Publication No. 97-44051, 1–154).

Another treatment technique uses dry powder medication as a substitute for aerosol medication. Children and elderly patients often find dry powder inhalers easier to use than MDI's. (Newman S. P., Weisz A. W., Talaee N., Clarke S. W., *Improvement Of Drug Delivery With A Breath-Activated Pressurized Aerosol For Patients With Poor Inhaler Technique.* Thorax, 1991, 4(46), 712–716). It is reported that inhaler induced symptoms are lower with some dry powder inhalers (dry powder budesonide and turbutan) as compared to MDI's. (Pauwels R. A., Hargreave F. E., Camus P., Bukoski M., Stahl E., *A 1-Year Study Of Turbohaler Vs Pressurized Metered Dose Inhaler In Asthmatic Patients,* Chest, July 1996, 110(1), 53–57). Certain dry powder inhalers are also reported to deliver more drug to the lungs than an equivalent aerosol inhaler. (Borgstrom L., Derom E., Stahl E., Wahlin-Boll E., Pauwels R., *The Inhalation Device Influences Lung Deposition And Bronchodilating Effect Of Terbutaline,* American Journal of Respiratory and Critical Care Medicine, May 1996, 153(5), 1636–1640). However, another study reported that dry powder inhalers deliver only 10% of the inhaled medication dose to the lungs. (Taburet A. M., Schmidt B., *Pharmacokietic Optimisation Of Asthma Treatment,* Pharmacokinetics, May 1994, 26(5), 396–418/ published erratum in August 1994, 27(2), 149)

Currently, there are also breath activated dry powder inhalers on the market. Dry powder breath activated inhalers do not rely on coordination between activation and inhalation and therefore are easier for the patient to use. However, existing dry powder inhalers, including breath activated devices, have a number of disadvantages. The medication dose is lost if a patient exhales through the device. (National Institutes of Health: National Heart, Lung, and Blood Institute. *Guidelines For The Diagnosis And Management Of Asthma,* July 1997, Bethesda, Md., NIH Publication No. 97-44051, 1–154). It is also necessary to inhale rapidly to use a dry powder inhaler properly. Id. Rapid inhalation may not be possible during an acute asthma exacerbation. (Boulet L. P., d'Amours P., Berube D., Rouleau M., Parent J. G., Pelletier C. & Touchette C., *Update On Inhalation Therapy In Asthma And Obstructive Bronchopulmonary Diseases,* Union Med. Canada, January 1994, 123(1), 23–31§). Thus, inspiratory flow may not be sufficient when medication is most needed.

Devices that do not rely on patient inhalation technique have an advantage in medication delivery for asthmatics. Spacers are one such device that is being promoted as a way to deliver aerosol from MDI's to the patient's lung without the need for skillful patient technique. Spacers used with MDI's also offer an advantage to MDI's alone in that less medication is deposited in the oropharynx, reducing local side effects. (National Institutes of Health: National Heart, Lung, and Blood Institute. *Guidelines For The Diagnosis And Management Of Asthma,* July 1997, Bethesda, Md., NIH Publication No. 97-44051, 1–154). Larger volume spacers (>600 cc) increase lung delivery in MDI's in patients with poor MDI technique. Id. This is due to the large droplets precipitating out in the spacer holding chambers prior to inspiration.

However, spacers also present certain disadvantages. Currently many spacers are being sold as universal for all aerosol canisters. A study found significant differences in the amount of drug available for inhalation when different spacers were used as inhalation aids with different drugs. (Barry P. W., O'Callaghan C., *Do Multiple Actuations Of Salbutamol MDI Into A Spacer Device Reduce The Amount Of Drug Recovered In Respirable Range?* European Respiratory Journal, September 1994, 7(9), 1707–1709). Spacers can also vary widely as to the amount of respirable dose delivered. (Iula, A. K., Flynn C. L., Delucca F., *Comparative Study Of The In Vitro Dose Delivery And Particle Size, Distribution, Characteristics Of An Azmacort Metered-Dose Inhaler In Combination With Four Different Spacer Devices,* Current Therapeutic Research, August 1997, 58(8), 544–554)

Another major problem with spacers is that multiple actuations into the volumetric spacer does not linearly increase the amount of drug available for inhalation. (Barry P. W., O'Callaghan C., *Do Multiple Actuations Of Salbutamol MDI Into A Spacer Device Reduce The Amount Of Drug Recovered In Respirable Range?* European Respiratory Journal, September 1994, 7(9), 1707–1709). The amount of medication within respirable particles decreases considerably following multiple activations into a spacer and with increasing residence times within the spacer before inhalation. (O'Callaghan C., Cant M., Robertson C., *Deliver Beclomethasone Dipropionate From A Spacer Device: What Dose Is Available For Inhalation,* Thorax, October 1994, 49(10), 961–964). Therefore, patients who pump repeatedly into a spacer during an acute attack to get additional medication, may mistakenly receive an insufficient dose.

Large volume spacers are also bulky, and medication export may be reduced in some devices after cleaning and by sanitization. (Bisgaard H., Anhoj J., Klug B., Berg E., *A Non-Electrostatic Spacer For Aerosol Delivery,* Arch. of Dic. Children, September 1995, 73(3), 226–230). Static electricity can also reduce spacer output. Id. Reduction in spacer output therefore may occur during conditions when asthma is exacerbated, such as cold dry weather.

For daily treatment of asthma symptoms, MDI's are the most common and widely prescribed medication delivery system for inhaled medications for asthmatics. Nearly all asthma sufferers depend on MDI's for disease control and symptomatic relief. Despite almost universal use of MDI's, a high percentage of users incorrectly employ MDI's.

The proper use of MDI's is complicated and requires the user/patient to perform the following steps: activation during early inspiration, adequate inspiratory flow, adequate breath holding and deep inhalation. (Goodman D. E., Israel E., Rosenberg M., Johnston R., Weiss St., Drazen J. M., *The Influence Of Age, Diagnosis, And Gender On Proper Use Of Metered-Dose Inhalers,* American Journal of Respiratory and Critical Care Medicine, November 1994, 150(5 Part 1), 1256–1261). The most frequent patient errors include: lack of coordination between activation and inspiration; absence of breath holding; and activation of the aerosol on more than one occasion during inspiration. (Boccuti L., Celano M., Geller R. J., Phillips K. M., *Development Of A Scale To Measure Children's Metered Dose Inhaler And Spacer Technique,* Annals of Allergy, Asthma and Immunology, September 1996, 77(3), 217–221). These errors adversely affect delivery of aerosol medication to the lower respiratory tract.

Improper inhaler technique and inadequate MDI design can lead to side effects from the inhaled medications. Corticosteroid inhalers are known to cause adrenal suppression in some asthmatic children. (Goldberg S., Algur N., Levi M., Brukheimer E., Hirsch H. J., Branski D., Kereem E., *Adrenal Suppression Among Asthmatic Children Receiving Chronic Therapy With Inhaled Corticosteroid With And Without Spacer Device,* Annals of Allergy, Asthma and Immunology, March 1996, 76(3), 234–238). This side effect is more common in patients inhaling directly from MDI's than those patients using a large volume spacer. Medication deposited in the oropharynx can lead to irritation, foul taste and thrush, which may cause the patient to avoid using the medication. Spacers/holding chambers decrease oropharyngeal deposition and reduce potential systemic absorption of inhaled corticosteroid preparations that have higher oral bioavailability. Without a spacer/holding chamber, approximately 80% of the dose from an MDI is swallowed. (National Institutes of Health: National Heart, Lung, and Blood Institute. *Guidelines For The Diagnosis And Managements Of Asthma,* July 1997, Bethesda, Md., NIH Publication No. 97-44051, 1–154). Spacer devices are reportedly useful in reducing local side effects in the oropharynx by decreasing deposits in the oropharynx by at least 90%.

One study reported that although MDI's are the most frequently prescribed type of inhaler, at least 50% of patients are unable to use these devices efficiently and 10 to 15% of those patients who can initially use the MDI efficiently later develop an inefficient technique. (Levitt M. A., Gambrioli E. F., Fink J. B., *Comparative Trial Of Continuous Nebulization Versus Metered-Dose Inhaler In The Treatment Of Acute Bronchospasm,* Annals of Emergency Medicine, September 1995, 26(3), 273–277). Another study showed that only 33.2% of adults and 26% of children used adequate technique (deep inspiration synchronized with inhaler activation, followed by breath holding for 5 seconds). (National Institutes of Health: National Heart, Lung, and Blood Institute. *Guidelines For The Diagnosis And Management Of Asthma,* July 1997, Bethesda, Md., NIH Publication No. 97-44051, 1–154). It was also shown that almost one half of the patients studied did not activate the MDI canister at the start of inhalation.

The main factor related to the improper use of MDI's is absence of previous instruction. (Benjaponpitak S., Kraisaarin C., Direkwattanachai C., Sasissakunporn C., *Incorrect Use Of Metered Dose Inhalers By Pediatric Residents,* Journal of the Medical Association of Thailand, February 1996 79(2), 122–126). Despite training by their physicians, several studies have demonstrated that many patients do not use MDI's or other inhaler devices correctly, and a simple training session is inadequate. Even with instruction, only 26% of instructed adults and 22.1% of instructed children used optimal technique. (Liard R., Zureik M., Aubier M., Korobaaaeff M., Henry C., Neukirch F., *Misuse Of Pressurized Metered Dose Inhalers By Asthmatic Patients Treated In French Private Practice,* Rev. Epidemiology Sante Publique, 1995, 43(3), 242–249). Unfortunately, instruction of MDI technique requires a significant time commitment and may not be feasible for all patients, especially those in an Emergency Department. (Selroos O., Lofross A. B., Pietinaalho A., Riska H., *Comparison Of Terbutaline And Placebo From A Pressurised Metered Dose Inhaler And A Dry Powder Inhaler In A Subgroup Of Patients With Asthma,* Thorax, Dec. 1994, 49(12), 1228–1230). It has also been demonstrated that the motor/technical skill necessary to properly use an MDI inhaler can deteriorate over time. (HealthScan, Inc. *Chances*

*Are: Handbook of Clinical Probabilities in Asthma.* 1997, 11(2) p.1–6; First Quarter)

Physicians themselves have been shown to possess inadequate knowledge of the correct use of inhalers with all types of devices. (Rebuck D., Dzyngel B., Khan K., Kesten R. N., Chapman K. R., *The Effect Of Structured Versus Conventional Inhaler Education In Medical Housestaff,* Journal of Asthma, 1996, 33(6), 385–393). Postgraduate teaching programs leave physicians to acquire inhaler-handling skills informally in the context of day-to-day patient care. Id. Many medical personnel responsible for monitoring and instructing patients in optimal inhaler utilization do not possess rudimentary skills with these devices. (Hanania N. A., Wittman R., Kesten S., Chapman K. R., *Medical Personnel's Knowledge Of And Ability To Use Inhaling Devices: Metered Dose Inhalers, Spacing Chambers, And Breath-Actuated Dry Powder Inhalers,* Chest, January 1994, 105(1), 111–116). Of seven recommended steps for correct MDI use, residents, on average, correctly performed only 3.8 of these steps. (Amirav I., Goren A., Pawlowski N. A., *What Do Pediatricians In Training Know About The Correct Use Of Inhalers And Spacer Devices?* Journal of Allergy and Clinical Immunology, October 1994, 94(4), 669–675)

In one study, second-year pediatric residents improperly timed the activation of the MDI 49% of the time, activating the MDI canister before starting inhalation. (Benjaponpitak S., Kraisaarin C., Direkwattanachai C., Sasissakunporn C., *Incorrect Use Of Metered Dose Inhalers By Pediatric Residents,* Journal of the Medical Association of Thailand, February 1996, 79(2), 122–126). Seasoned physicians do not fare much better. In a survey, only 55% of faculty members correctly answered at least three of the seven steps necessary for proper inhaler technique, though all prescribed MDI's for their patients. (Hira H. S., *Faulty Use Of Metered Dose Inhalers By Physicians,* Journal of Assoc. of Physicians in India, July 1994, 42(7), 520, 524–525). While educational sessions may somewhat improve performance, education is not sufficient to guarantee perfect MDI technique. (Resnick D. J., Gold R. L., Lee-Wong M., Feldman B. R., Ramakrishnana R., Davis W. J., Annals of Allergy, Asthma Immunology, February 1996, 76(2), 145–148). A single training session using videotaped MDI demonstrations was shown to be inadequate in teaching pharmacists and pulmonary fellows to evaluate MDI technique. (Farr S. J., Rowe A. M., Rubsamen R., Taylor G.,*Aerosol Deposition In The Human Lung Following Administration From A Microprocessor Controlled Pressurized Metered Dose Inhaler,* Thorax, June 1995, 50(6)639–644)

If physicians and other health care personnel do not know how to use inhalers and have difficult leaning proper technique, there is little chance that they can teach the patients proper technique.

In order to overcome some of the problems with poor MDI technique, aerosol breath activated inhalers are currently available. One such device is shown to require more rapid inspiration to activate than is optimal for deposition of medication into the lungs. (National Institutes of Health: National Heart, Lung, and Blood Institute. *Guidelines For The Diagnosis And Management Of Asthma,* July 1997, Bethesda, Md., NIH Publication No. 97-44051, 1–154). The device also clicks loudly on actuation, and patients may reflexively stop inhalation upon hearing the click, preventing the full dose of medication from getting to the lungs. Id.

Optimal design of an MDI for a specific agent also requires precise calculation based on particle size and other physiochemical characteristics of the particular medication compound as it relates to the desired dose to be activated from the MDI spraythead. The respirable dose is commonly defined as total dose with particle size <5.8 micrometer. (Iula, A. K., Flynn C. L., Delucca F., *Comparative Study Of The In Vitro Dose Delivery And Particle Size, Distribution, Characteristics Of An Azmacort Metered-Dose Inhaler In Combination With Four Different Spacer Devices,* Current Therapeutic Research, August 1997, 58(8), 544–554)

One MDI study showed that firing with a medium inspiratory flow rate (90 liters/minute) and early in the cumulative inspired volume (<300 ml) resulted in the highest lung deposition, at 18.6%. (Farr S. J., Rowe A. M., Rubsamen R., Taylor G., *Aerosol Deposition In The Human Lung Following Administration From A Microprocessor Controlled Pressurized Metered Dose Inhaler,* Thorax. June 1995, 50(6), 639–644). Unfortunately, 60% of asthma patients inhale at less than 60 liters/minute, and during acute attacks their flow rate may be less. (Newman S. P., Sted K. P., Resader S. J., Hooper G., Ziereniberg B., *Efficient Delivery To The Lungs Of Flunisolide Aerosol From A New Portable Hand-Held Multi-Dose Nebulizer,* Journal of pharm. Science, September 1996, 85(9), 960–964). Thus, an ideal device needs to be adaptable to fire even with very low flow rates, because it is at times like these that the asthma patient needs medication relief most desperately.

In addition to the problems identified above, one study found that insufficient hand strength was also a significant cause of the elderly not being able to use MDI's, which require the patient to apply manual pressure to the top and bottom of the device to activate it. (Gray S. L., Williams D. M., Pulliam C. C., Sirgo M. A., Bishop A. L., Donohue J. F., *Characteristic Predicting Incorrect Metered Dose Inhaler Technique In Older Subjects,* Archives of Internal Medicine, May 1996, 156(9), 984–988). An ideal MDI would require minimal hand strength so that both children and elderly could easily use the device.

Patients often run out of inhaler medication because they can not estimate how much medication remains in the canister. This is because they depend on inaccurate methods of estimation, such as shaking the inhalers and listening to the contents, estimating the weight of the canisters, and observing the size of the emissions.

Rapid serial reactivation of MDI's also reduces respirable dose by 15 to 18%. (Everard M. L., Devadason S. G., Summers Q. A., LeSouef P. N., *Factors Affecting Total And "Respirable" Dose Delivered By Salbutamol Metered Dose Inhaler,* Thorax, July 1995, 50(997), 746–749). An interval between actuation of at least 5 seconds is considered necessary to consistently deliver full doses. Id.

Additives in MDI's such as inert ingredients including propellant can cause bronchoconstriction in some patients with asthma. (Shaheen M. Z., Aayres J. G., Benincasa C., *Incidence Of Acute Decreases In Peak Expiratory Flow Following The Use Of Metered Dose Inhalers In Asthmatic Patients,* European Respiratory Journal, December 1994, 7(12), 2160–2164)

An open-mouth technique with MDI's, whereby the MDI is manually activated and coordinated with inhalation while the MDI is in proximity but not in direct contact with the patient's mouth, has been shown to lead to enhanced drug delivery to the lung compared to the conventional closed-mouth technique. (National Institutes of Health: National Heart, Lung, and Blood Institute. *Guidelines For The Diagnosis And Management Of Asthma,* July 1997, Bethesda, Md., NIH Publication No. 97-44051, 1–154). None of the current breath activated inhalers are usable with an open-mouth technique, however, and the open-mouth technique is difficult to master.

Thus, there are a number of disadvantages that are not addressed by current MDI's, spacers and breath-activated devices.

SUMMARY OF THE INVENTION

It is thus an object of the present invention to provide a device for dispensing medication into the respiratory tract that provides an integral open-mouth technique position and a closed-mouth technique position.

It is a further object of the present invention to provide a device for dispensing air-mixed medication into the respiratory tract that provides different air to medication ratios depending on whether the open-mouth technique position or closed-mouth technique position is used.

It is a further object of the present invention to provide a breath-activated device for dispensing air-mixed medication into the respiratory tract that provides an electro-mechanical discharge and uses a battery on a disposable canister as the power supply.

It is a further object of the present invention to provide a device for dispensing air-mixed medication into the respiratory tract that has first and second air-mixing channels.

It is a further object of the present invention to provide a device for dispensing air-mixed medication into the respiratory tract that has an airflow sensor in a first air channel for sensing inhalation and a second air channel that is opened during dispensing of the medication.

It is a further object of the present invention to provide a device for dispensing air-mixed medication into the respiratory tract that dispenses liquid medication.

It is a further object of the present invention to provide a device for dispensing air-mixed medication into the respiratory tract that dispenses dry medication.

It is a further object of the present invention to provide a device for dispensing air-mixed medication into the respiratory tract that has a medication dosage regulator.

It is a further object of the present invention to provide a device for dispensing air-mixed medication into the respiratory tract that has an indicator of remaining medication dosage, or usage recorder.

It is a further object of the present invention to provide a device for dispensing air-mixed medication into the respiratory tract that is manually cocked.

It is a further object of the present invention to provide a device for dispensing air-mixed medication into the respiratory tract that has a sound deadeninig device acting after breath activation.

It is a further object of the present invention to provide a device for dispensing air-mixed medication into the respiratory tract that has a battery located on or associated with a replaceable medication canister that is used to power other functions of the device.

These and other objects of the present invention will be apparent to those of ordinary skill after review of the specification and claims in view of the figures.

DETAILED DESCRIPTION

The present invention is a breath-activated inhaler intended to address the disadvantages of the previously described MDI's, spacers, and breath-activated devices. In a preferred embodiment. the device is constructed primarily of plastic, and includes various electrical components that are battery powered.

Preferably, the invention is electronically, activated, and employs a microprocessor chip, which is integral with each medication canister. The microprocessor chip controls activation based on flow rate and time interval from start of inspiration. This allows the same device to be used with different medications but allows each medication to be optimally delivered.

The invention may also be electro-mechanically activated, using, an electrical solenoid to release a spring mechanism.

The invention may also incorporate an electronic digital counter. The counter is part of a replaceable medication canister that has an attached chip and battery power supply to store information on remaining medication doses. The counter thus provides valuable information to both patient and physician, reducing the incidence of patients running out of medication. Placing the battery on the replaceable canister also ensures that a fresh battery will always be available.

The microprocessor employed in the invention may incorporate a time delay to prevent rapid successive actuations and thus preventing over medication. A time delay also serves to discourage patients from "mock-activating" the device with rapid successive actuations.

The invention may also incorporate a bleed hole in the nozzle. This feature, in conjunction with a venturi design, allows more complete atomization of the medication. Smaller droplets (<5 micrometers) can be carried further along a current of air and thus will minimize oropharynx deposition.

The invention may also incorporate a tube within a tube design in the mouthpiece. This two position mouthpiece simulates an open-mouth technique using conventional closed-mouth technique. Oropharynx deposition is decreased with this open-mouth technique. With convention MDI's, closed-mouth technique requires far less motor skill than open-mouth technique. With the present invention, the same technique is used for both closed and open-mouth features. For patients unable to generate sufficient inspiration flow to trigger the device using this open-mouth technique, the patient can put his/her lips around the proximal most part of the mouthpiece to use ordinary closed-mouth inhalation.

Figure 1:
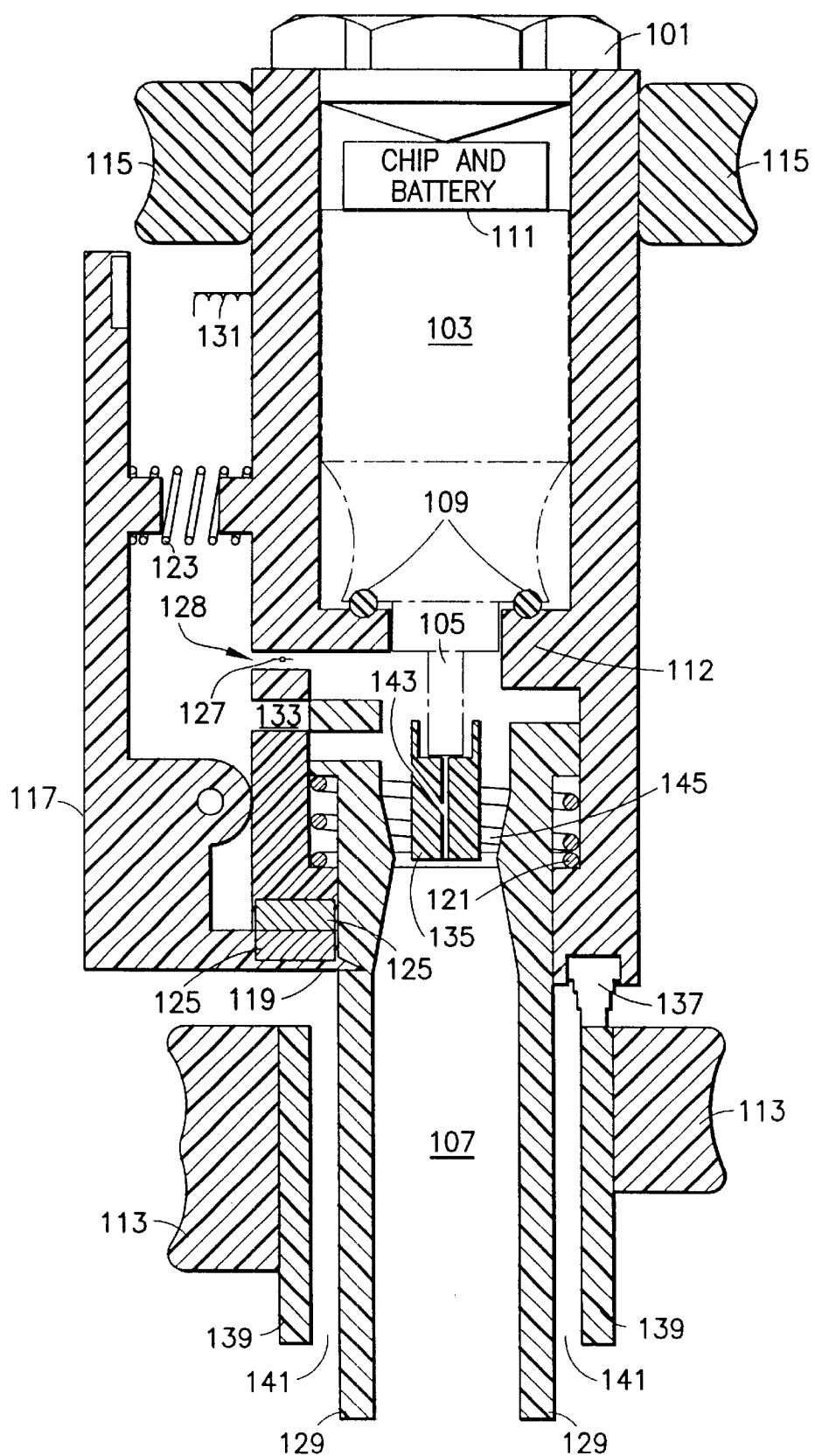
FIG. 1 illustrates one embodiment of the invention in the cocked position.

The features described above will now be described above in greater detail. Referring first to FIG. 1, the invention is illustrated in the cocked, or primed configuration. To operate the device, a cap 101 is removed and a metered-dose inhaler canister 103 is inserted into an opening. The canister has a nozzle 105 that is directed toward a mouthpiece 107. The nozzle of the metered-dose canister is preferably sealed against the bottom of the compartment by a ring gasket 109. Once the canister is properly oriented, cap 101 is replaced. Preferably, the canister has electrical circuitry or microprocessor chip and a battery 111 that are constructed so as to form an integral element of the canister. This has an advantage of providing a fresh battery when the canister is changed. One function of the circuitry and battery is to operate the electro-mechanical components of the inhaler when breath-activated. This function can be considered to be a medication dosage regulator in that a dose of medication is only dispensed when the electro-mechanical components operate. Another function of the circuitry and battery is to collect and record information on how many times the device has been used and thereby also determine how many inhalations or doses remain in the canister. This function can be considered a usage recorder, as the use information is collected and recorded as the device is used or activated. The circuitry that is used to collect and record information on how many time the device has been used can also function to determine or indicate the remaining medication dosage in the canister. Canisters are manufactured with a known quantity of medication and the quantity that is dispensed during each use is also known. Therefore, it is a simple matter to calculate the remaining medication dosage. It is preferred, but not necessary that these functions described above be performed.

To place the device in the primed position, as illustrated in the embodiment of FIG. 1, the mouthpiece 107 is extended from the main body of the device 112 by holding fingergrips 113 and 115 and pulling them apart until a cantilever latch 117 engages a retainer 119 on the mouthpiece. By extending the mouthpiece from the main body and latching it into that position, a spring 121 is placed in compression. The cantilever latch 117 is held in the cocked position by another spring 123, which also keeps the latch 117 and retainer 119 properly oriented. In the figure, the retainer 119 has been illustrated as engaging a v-shaped notch, but other shapes or arrangements that provide a positive engagement with an ability to release would be suitable.

In the cocked position, a set of electrical contracts 125 are in contact with each other, forming an electrically conducting contact, or switch. In this orientation, current may flow through from one contact to the other contact, completing a circuit. In a preferred embodiment, this circuit forms part the electro-mechanical circuitry of the device. In particular, the contacts 125 may be connected to a flow sensor 127 that serves to detect inhalation by the patient.

Flow sensor 127 is located in an opening 128 that serves to connect the mouthpiece to ambient air. In the cocked position opening 128 is the only opening between the mouthpiece and ambient air. Thus, when a patient places his or her mouth around the mouthpiece, at position 129, and inhales, all air must flow through the opening 128 and past the flow sensor 127.

When the patient uses the open-mouth position 139 which is described in greater detail below, less than all the air must flow through the opening 128 and past the flow sensor 127. This is not a problem as the flow sensor has sufficient sensitivity to detect the inhalation flow and actuate the device even when less that all the air flow passes the flow sensor.

In the preferred embodiment, the flow sensor 127 is a flow-sensing resistor. In an alternative embodiment, the flow sensor may be a crystal whose resistance is thermally sensitive. Other alternative embodiments for the flow sensor, including but not limited to a mechanical vane and switch, are also possible and suitable.

After the device is cocked, as described above, the patient holds the device by fingergrips 113 in preparation for activation. He then places the end of the mouthpiece 107 in his mouth and wraps his lips around the opening at position 129. The patient then simply inhales. As previously described, when the patient inhales, he draws air through the mouthpiece across the flow-sensor 127. When the flow sensor is a resistor, the air flow causes the resistor to cool. The reduced temperature causes resistance across the resistor to drop, causing more current to flow across it according to Ohm's law. Appropriate circuitry senses this change in current, acting as a switch.

Figure 2:
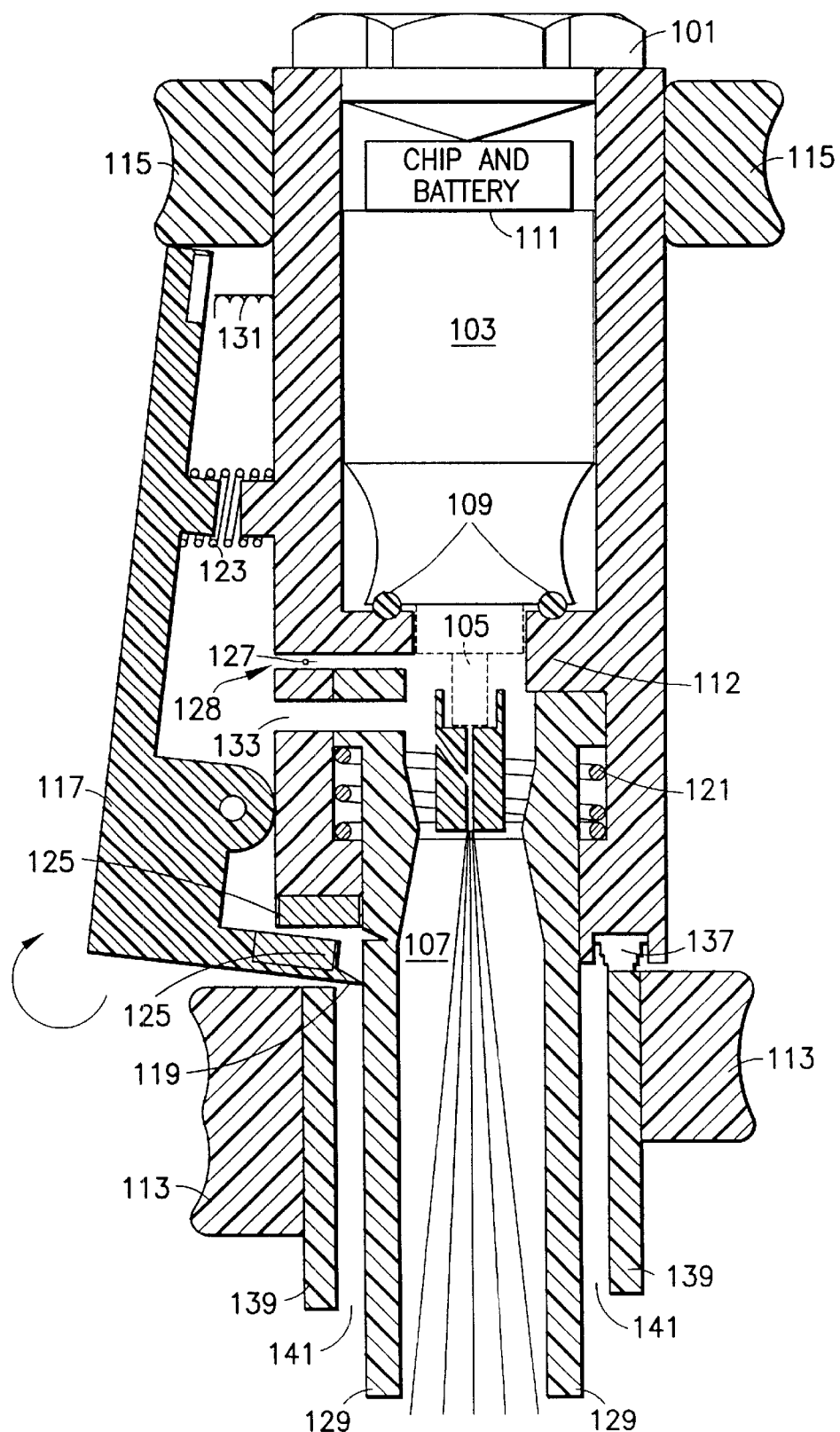
FIG. 2 illustrates embodiment of the invention of FIG. 1 immediately after breath-activation.
Figure 3:
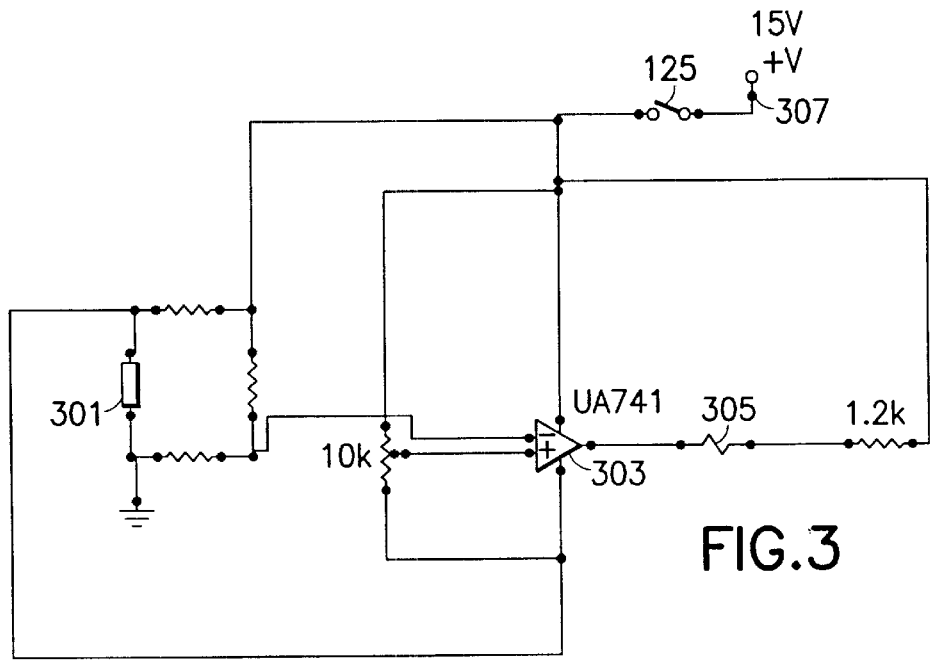
FIG. 3 illustrates an embodiment of electrical circuitry for electro-mechanical activation of the device using a crystal flow sensor.

Referring, now to FIG. 2. this switching action activates a solenoid 131 which moves the cantilever latch 117, releasing the retainer 119, and thereby allowing spring 121 to move mouthpiece 107 relative to the main body 112 of the device. When it moves, the end of mouthpiece 107 pushes or depresses the nozzle 105 of the metered-dose inhaler canister 103, releasing aerosolized medication through an opening into the mouthpiece 107 where it is then inhaled by the patient, eventually coming to rest in the lungs.

In a preferred embodiment, when the solenoid 131 is activated and the mouthpiece 107 moves relative to the main body 112 of the device, a gated air channel 133 is opened, providing less restriction of inhalation air flow and allowing a greater quantity of air to be mixed with the aerosol.

The device has been described thus far with reference to a closed-mouth technique. In another embodiment, the device may be used to achieve the beneficial results of an open-mouth technique. Referring to FIG. 1, a second mouth position 139 is available. Using this second mouth position, the patient places his or her lips around an outer tube and inhales. In this second mouth position, an additional air channel 141 is available.

Open-mouth technique has been prescribed and used wraith conventional MDI. Open-mouth technique with a conventional MDI requires the patient to hold the inhaler a few inches from the mouth, and activate the MDI in coordination with inhalation. Using this conventional open-mouth technique, the patient inhales additional air, but the amount of medication that is deposited in the mouth and oropharynx is less. When open-mouth technique is correctly performed, more medication is carried to and deposited in the lungs and less medication is deposited in the mouth and back of the throat. The mechanism for this improvement in medication administration is unclear. One possible explanation is that with open-mouth technique, the air column that is inhaled is not uniform and the medication is more concentrated in the center of the column. In this manner, the medication in the center of the column may be somewhat shielded and therefore less likely to contact the mouth or back of the throat before being fully inhaled. It is also possible that the additional air inhaled with open-mouth technique simply alters the medication-to-air ratio and thereby reduces the incidence of medication deposit in the mouth or throat. Regardless of the reason, properly performed open-mouth technique provides a significant treatment advantage. To provide ease of description within this specification, the open-mouth technique is presumed to result in a different medication-to-air ratio than closed-mouth technique.

With a traditional breath-activated device, the use of open-mouth technique, where the patient holds the device away from the lips, might not provide sufficient flow to actuate the device. However, the present invention is more sensitive to flow by using the gated channel. Thus, a patient with poor inspiration flow rate is still able to breath activate the device using the open-mouth position of the present invention.

It should be noted that while the terms "open-mouth" and "closed-mouth" are used in this description, in both cases, the patient will make lip contact with the device. The difference is that for the open-mouth technique, the patient uses the outer opening 139 and for the closed-mouth technique, the patient uses the inner opening 129. With a conventional MDI, the only way to perform open-mouth technique is to keep the lips from contacting the MDI. With the present invention, a patient is able to achieve the beneficial result of an open-mouth technique using a device that is operated with the lips contacting the mouthpiece as in a closed-mouth device.

Referring again to FIG. 1, in a preferred embodiment, there is also a bleed hole 143 in the nozzle 135. The placement of this bleed hole and an accompanying venturi effect provided by a constriction of the air passage 145, allows air to mix with the medication while in the nozzle, emulsifying the medication before it is ejected from the nozzle 135. This additional air mixing of the medication, while in the nozzle, further ensures that the medication is aerosolized into fine droplets.

In a preferred embodiment, a short time after the device has been discharged by breath-activation (preferably about 10 seconds), the device makes an audible tone, using the circuitry and battery power, signaling to the patient that he can release his breath.

As illustrated in FIG. 2, once the device has been discharged or breath-activated, the contacts 125 no longer make electrical contact. In this "open" position, the contacts can serve to prevent battery drain. Once discharged, no further medicine can be accidentally released until the device is cocked or primed again. This "open" or uncocked position is a storage position for the device.

After each activation, a digital counter shows the number of inhalations remaining in the canister 103. In a preferred embodiment, the device also has a timer delay to prevent a second activation before one minute (or another preset period of time) has elapsed. This time delay allows the canister to deliver a full dose in a second activation.

As previously described, it takes only a few seconds to cock the device. Release of the medication into the lungs after breath activation takes milliseconds.

The device of the present invention is preferably much more sensitive to inhalation than conventional breath-activated devices. This increased sensitivity is achieved by using the gated channel (133 in FIGS. 1 and 2) that opens only after activation. This arrangement allows all airflow to pass over the air flow sensor when in the cocked position and will provide activation with a flow rate as low as 2 liters/minute. This capability for low flow rate activation can be critical for a patient with minimal inspiratory flow during an asthma attack.

To prevent the loud click on activation that is heard in the use of some breath-activated devices, the invention may also include a dashpot 137 to dampen the initial motion of the mouthpiece 107 relative to the main body 112. The dashpot thus serves as a sound-dampening device to deaden the sound and reduces noise made during activation.

This device can be manually activated in an emergency in the unlikely case the batteries on the canister runs out of power or there is an electronic malfunction. A cover (not illustrated) over the canister is easily removable to allow manual actuation but a tear sensitive tape will alert the health professional that the device has been tampered with. This, along with the timer delay described above, also discourages the practice known as dumping, where the patient repeatedly and rapidly discharges the MDI, usually just prior to an appointment in an attempt to hide his or her failure to follow the prescribed medication schedule.

As described above, the device is easy to use. requiring minimal hand strength to cock and only inhalation for activation. This can be very important to persons with arthritis, or to the individual with poor physical conditioning, The device is also intuitive to use, so the patient needs minimal instruction. A simple three-step operation is needed to use the inhaler: shake, pull out the ends of the inhaler by holding the fingergrips, and then inhale. Electronics allows additional optional enhancements such as voice prompts to remind the patient to shake the canister, pull it apart, inhale and when to exhale.

Referring to FIG. 3, an embodiment of an electrical circuit for electro-mechanical activation is illustrated. The circuit includes a flow sensor 301, and an op-amp 303 to drive a solenoid 305. The contacts 125 that are illustrated in FIGS. 1 & 2 are also illustrated. A battery 307, to power the device is also illustrated. Parts of the circuit illustrated in FIG. 3, including the battery and op-amp, may be the same chip and battery that is illustrated at 111 in FIGS. 1 & 2.

Though not illustrated, conventional electronic circuitry, as would be known to one of ordinary skill in the art, are included in the embodiment described above that regulates the medication dosage by monitoring flow rate and time between start of inspiration. Similarly, circuitry to detect and record usage is included in another embodiment. This circuitry may record each use, subtracting it from a pre-set value associated with a full canister and testing the value to see if it has reached zero. Alternatively, the circuitry may record each use and add it to an initial value then test the value to see if it has reached a pre-set value, representing the total number of doses in the canister. In this manner the circuitry may indicate doses used, or doses remaining.

Though not illustrated, the conventional electronic circuitry may also record secondary information relating to use, such as date and time of use, or time since last use, or any other type of information relating to use that would help the patient or physician in treatment of the disease.

As illustrated in FIGS. 1, 2 and 3 the present invention combines a number of advantages into a single device. However, there are aspects of the invention that are adaptable to conventional MDI. For example, FIG. 4 illustrates an embodiment of the invention that incorporates the open-mouth technique with a conventional MDI. In FIG. 4, a conventional MDI mouthpiece 129 is surrounded by a second mouthpiece 139, which enables the open-mouth technique. In this embodiment, the patient is only able to place their lips on the outer mouthpiece and must therefore use the device in the open-mouth configuration. By providing an MDI of this design, the patent achieves the advantages of open-mouth technique with only a slight modification of the conventional MDI.

In another example of the invention, FIG. 5 illustrates a two-position mouthpiece allowing open-mouth and closed-mouth technique with an otherwise conventional MDI. In this embodiment, a first closed-mouth position, similar to the mouth position of a conventional MDI, is illustrated at 129. In addition to the closed-mouth position, the invention also provides an open-mouth position 139. With this combination of mouth positions, the invention provides the advantages of open-mouth and closed-mouth technique in an MDI that is only slightly modified.

From the previous examples, it is understood that a two-position mouthpiece, providing the benefits of open-mouth and closed-mouth technique, are accomplished in a number of different embodiments.

Figure 6:
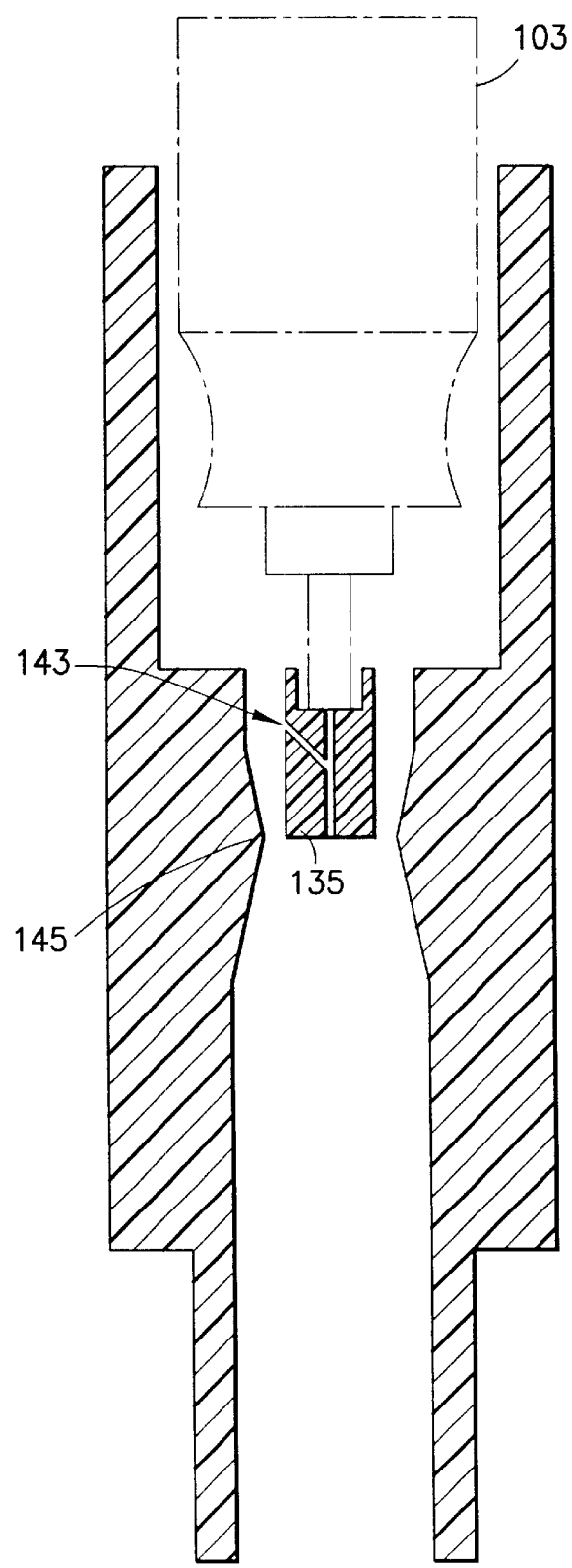
FIG. 6 illustrates an embodiment of the invention providing a bleed hole.

In another example of the invention, FIG. 6 illustrates a bleed hole 143 that provides enhanced emulsification. This is accomplished with a slightly modified MDI. The combination of bleed hole 143 and venturi 145, illustrated in FIG. 6 is readily adaptable to otherwise conventional MDI and provides better emulsification of the aerosol medication than is available with conventional MDI. The venturi 145 provides an area of low pressure that, in conjunction with the bleed hole 143, ensures greater mixing and emulsification of the medication than is available with convention MDI.

Figure 7:
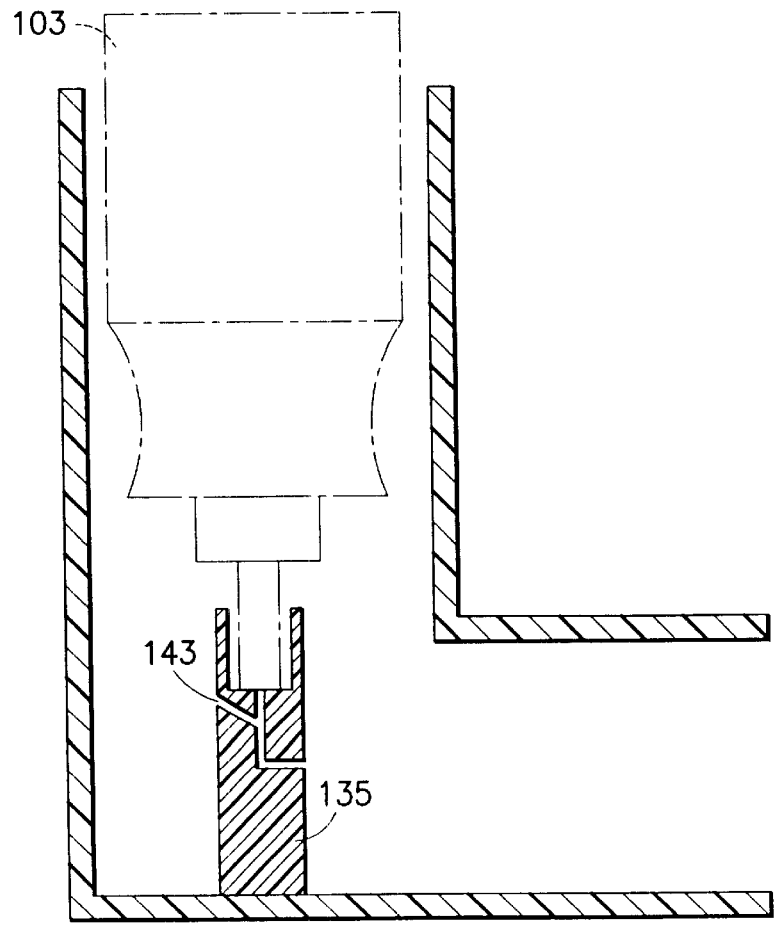
FIG. 7 illustrates a further embodiment of the invention providing a bleed hole.
Figure 4:
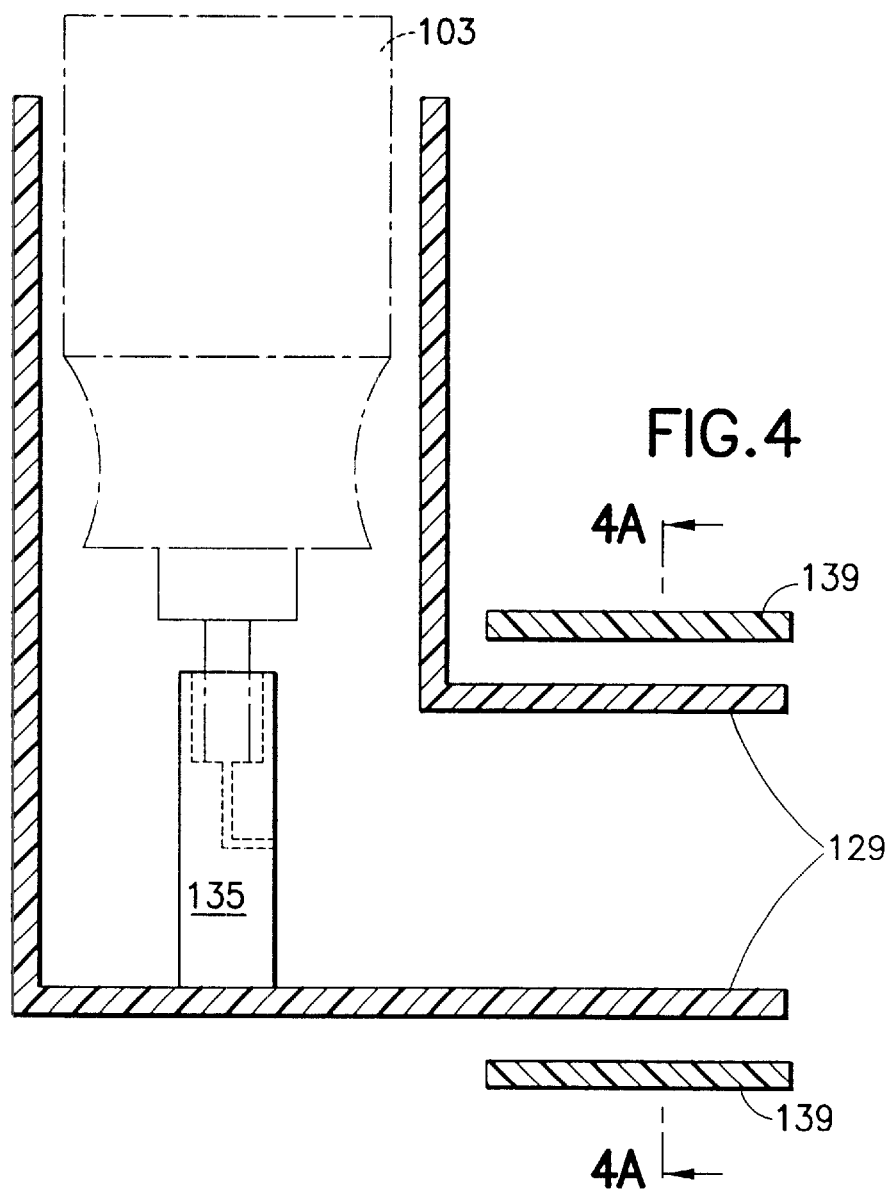
FIG. 4 illustrates an embodiment of the invention providing an open mouth position.
Figure 4A:
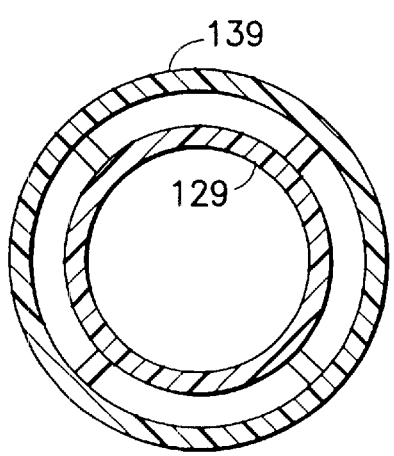
FIG. 4A illustrates a cross-sectional view taken along line 4A—4A in FIG. 4 of the mouthpiece in FIG. 4.
Figure 5:
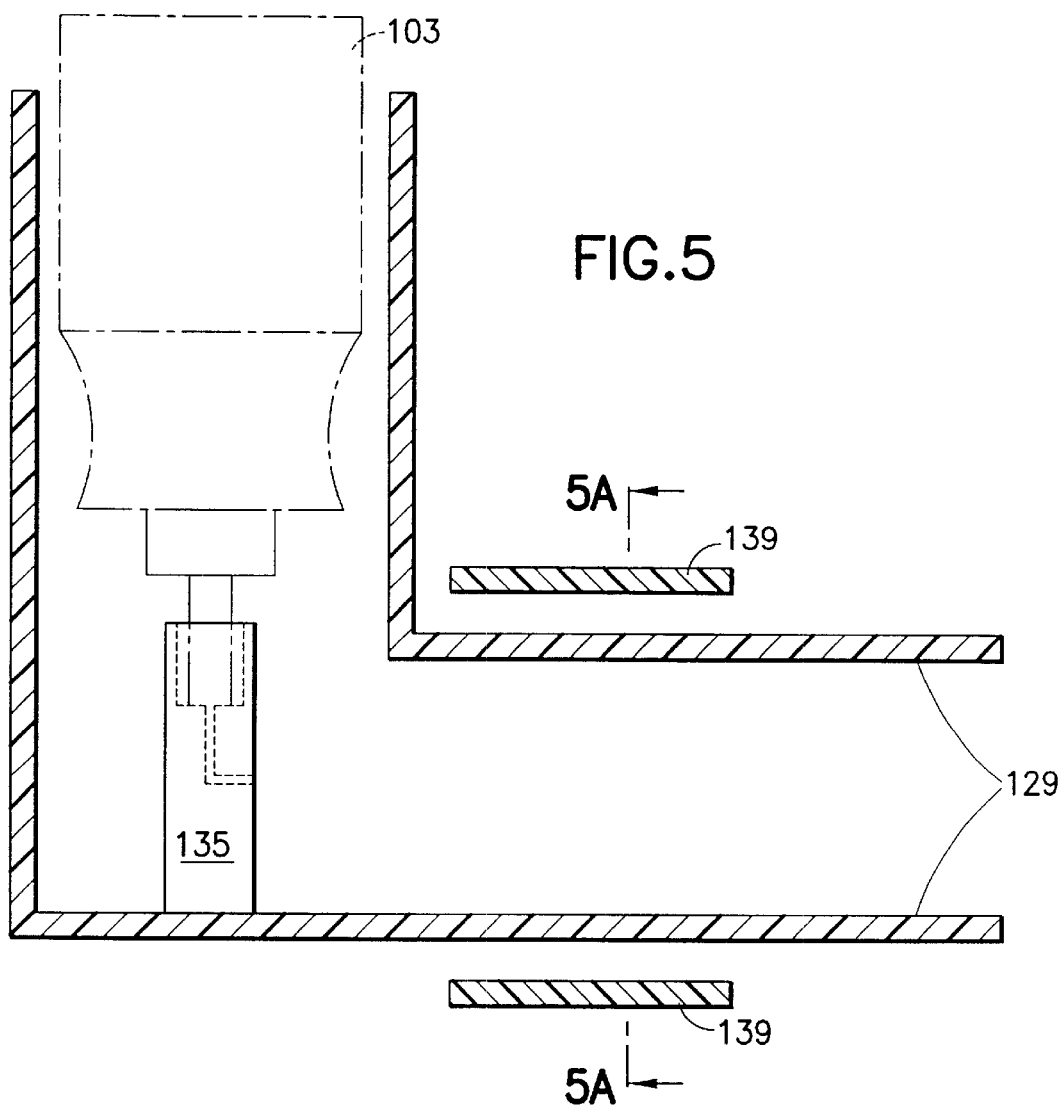
FIG. 5 illustrates an embodiment of the invention providing open and closed mouth position.
Figure 5A:
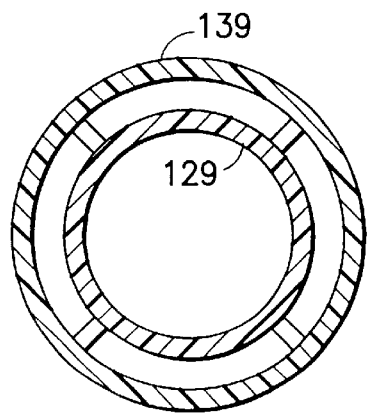
FIG. 5A illustrates a cross-sectional view taken along line 5A—5A in FIG. 5 of the mouthpiece in FIG. 5.

FIG. 7 illustrates another embodiment of the present invention where the bleed hole 143 is not closely associated with a structure that is specifically designed as a venturi, but the relationship between the structure of the MDI and the bleed hole otherwise provides for pressure differentials and thereby allows enhanced emulsification and mixing compared to that which is available without the bleed hole.

The invention has been described with reference to a number of preferred embodiments with accompanying figures as examples. However, it will be apparent to those of ordinary skill in the art that different aspects or embodiments of the invention may be accomplished independently of each other and that other embodiments, not expressly described in the specification, will achieve the objectives of the invention. As such, embodiments that accomplish the objectives of the invention are equally suitable and are understood to be disclosed by this specification even if not expressly described in the specification.

I claim:

1. A breath-activated apparatus that can be used by asthmatics during an asthmatic attack comprising:

a medication disposed in a medication holding canister;

a microprocessor chip and a power source disposed on the canister for powering activation of the apparatus, and for collecting and recording information concerning dosage in the canister;

an airflow sensor in a first air channel for sensing inhalation from a user with inhibited inspiratory flow, the sensor having a resistor that drops in resistance when airflow passes over the sensor such that the sensor has sufficient sensitivity to detect inhalation and actuate the apparatus independent of the amount of airflow inhaled that passes over the sensor;

a mouth piece for delivering the medication, the mouth piece is in communication with a flow sensor and the first air channel, such that the first air channel provides an unimpeded air flow path over the airflow sensor; and a second air channel in communication with the medication such that the second air channel is opened only during dispensing of the medication to assist in air-mixing the medication.

2. The apparatus of claim 1 wherein the medication comprises liquid medication.

3. The apparatus of claim 1 wherein the medication comprises dry medication.

4. The apparatus of claim 1 further comprising:

a first position on the mouthpiece; and a second position on the mouthpiece such that when the medication is taken from the first position a first medication-to-air ratio is given and when medication is taken from the second position a second medication-to-air ratio is given.

5. The apparatus of claim 4, wherein the first ratio is different from the second ratio.

6. The apparatus of claim 1 further comprising a medication dosage regulator.

7. The apparatus of claim 1 further comprising an indication of remaining dosage in a canister containing the medication.

8. The apparatus of claim 1 further comprising a usage recorder.

9. The apparatus of claim 1 wherein, the sensor produces a signal in response to a breath.

10. The apparatus of claim 9 wherein the power source is a battery forming a unitary structure with the canister containing the medication.

11. The apparatus of claim 1 further comprising a mechanical actuator for manual cocking prior to breath activation.

12. The apparatus of claim 1 further comprising a sound-dampening device acting after breath activation.

13. The apparatus of claim 12 wherein the sound-dampening device is a dashpot.

* * * * *